United States Patent
Schostek et al.

(10) Patent No.: US 12,245,748 B2
(45) Date of Patent: Mar. 11, 2025

(54) ENDOSCOPIC CAPSULE SYSTEM WITH HAPTIC FEEDBACK

(71) Applicant: Ovesco Endoscopy AG, Tübingen (DE)

(72) Inventors: Sebastian Schostek, Tübingen (DE); Marc Schurr, Tübingen (DE)

(73) Assignee: Ovesco Endoscopy AG (DE)

( * ) Notice: Subject to any disclaimer, the term of this patent is extended or adjusted under 35 U.S.C. 154(b) by 407 days.

(21) Appl. No.: 17/762,550

(22) PCT Filed: Sep. 23, 2020

(86) PCT No.: PCT/EP2020/076623
§ 371 (c)(1),
(2) Date: Mar. 22, 2022

(87) PCT Pub. No.: WO2021/058601
PCT Pub. Date: Apr. 1, 2021

(65) Prior Publication Data
US 2022/0354349 A1    Nov. 10, 2022

(30) Foreign Application Priority Data

Sep. 25, 2019 (EP) .................. 19199675

(51) Int. Cl.
*A61B 1/00* (2006.01)
*A61B 1/04* (2006.01)
(Continued)

(52) U.S. Cl.
CPC .......... *A61B 1/00158* (2013.01); *A61B 1/041* (2013.01); *A61B 5/6861* (2013.01); *A61B 5/062* (2013.01)

(58) Field of Classification Search
CPC ... A61B 1/00158; A61B 1/041; A61B 5/6861; A61B 5/062
See application file for complete search history.

(56) References Cited

U.S. PATENT DOCUMENTS

| 5,332,181 A | 6/1994 | Schweizer et al. |
| 9,888,966 B2 * | 2/2018 | Farritor ................. A61B 34/76 |

(Continued)

FOREIGN PATENT DOCUMENTS

| CN | 102307536 A | 1/2012 |
| CN | 103327884 A | 9/2013 |

(Continued)

OTHER PUBLICATIONS

Japanese Notice of Reasons for Refusal for Japanese Application No. 2022-519256, dated May 12, 2023 with translation, 7 pages.

(Continued)

*Primary Examiner* — Baisakhi Roy
(74) *Attorney, Agent, or Firm* — Buchanan Ingersoll & Rooney PC

(57) ABSTRACT

An endoscopic capsule system comprising: an endoscopic capsule having magnetic characteristics; an extracorporeal guiding and moving apparatus having a moveable multi-hinged cantilever arm which is pivotably mounted at a support stand at one end and at an effector having magnetic characteristics at the other end to move the endoscopic capsule in accordance with movement of the effector; a controller device to define the position and orientation of the endoscopic capsule relative to the effector, and a force and/or moment generation device or a braking device to generate counter forces and/or counter moments or braking forces against moving and/or guiding forces that are manually applied to the cantilever arm and/or effector in accordance with the actually defined position and/or orientation of the endoscopic capsule relative to the effector.

15 Claims, 4 Drawing Sheets

(51) Int. Cl.
*A61B 5/00* (2006.01)
*A61B 5/06* (2006.01)

(56) References Cited

U.S. PATENT DOCUMENTS

| | | | |
|---|---|---|---|
| 10,743,949 B2* | 8/2020 | Farritor | B25J 9/1602 |
| 2005/0075536 A1* | 4/2005 | Otsuka | A61B 90/50 |
| | | | 600/102 |
| 2007/0191671 A1 | 8/2007 | Kawano et al. | |
| 2008/0091070 A1* | 4/2008 | Dario | A61B 1/041 |
| | | | 600/118 |
| 2010/0113874 A1* | 5/2010 | Quirini | A61B 1/00156 |
| | | | 600/109 |
| 2011/0184235 A1 | 7/2011 | Schostek et al. | |
| 2012/0022328 A1 | 1/2012 | Reinschke | |
| 2012/0226092 A1 | 9/2012 | Kawano et al. | |
| 2013/0110128 A1* | 5/2013 | Schostek | B25J 19/0008 |
| | | | 606/130 |
| 2013/0172671 A1* | 7/2013 | Rentschler | A61B 1/0011 |
| | | | 156/247 |
| 2015/0018614 A1* | 1/2015 | Duan | A61B 1/041 |
| | | | 600/109 |
| 2015/0342501 A1* | 12/2015 | Di Natali | A61B 5/07 |
| | | | 600/424 |
| 2017/0156574 A1 | 6/2017 | Kawano | |
| 2017/0360283 A1 | 12/2017 | Kimura et al. | |
| 2019/0365210 A1 | 12/2019 | Duan et al. | |

FOREIGN PATENT DOCUMENTS

| | | |
|---|---|---|
| CN | 106659366 A | 5/2017 |
| DE | 102011054910 A1 | 5/2013 |
| EP | 2347699 A1 | 7/2011 |
| JP | 2011147785 A | 8/2011 |
| JP | 2012152607 A | 8/2012 |
| WO | 2009107892 A1 | 9/2009 |
| WO | 2014113697 A1 | 7/2014 |
| WO | 2016098818 A1 | 6/2016 |
| WO | 2019228533 A1 | 12/2019 |

OTHER PUBLICATIONS

Extended European Search Report for European Application No. 19 199 675.0, dated Mar. 23, 2020, 8 pages.
International Search Report and Written Opinion for Application No. PCT/EP2020/076623, dated Dec. 17, 2020, 10 pages.
European Communication under Rule 71(3) for European Application No. 19 199 675.0, dated Feb. 8, 2023, 9 pages.
Office Action (The First Office Action) issued Oct. 17, 2024 by the State Intellectual Property Office of People's Republic of China in corresponding Chinese Patent Application No. 202080067614.5 and an English translation. (10 pages).

* cited by examiner

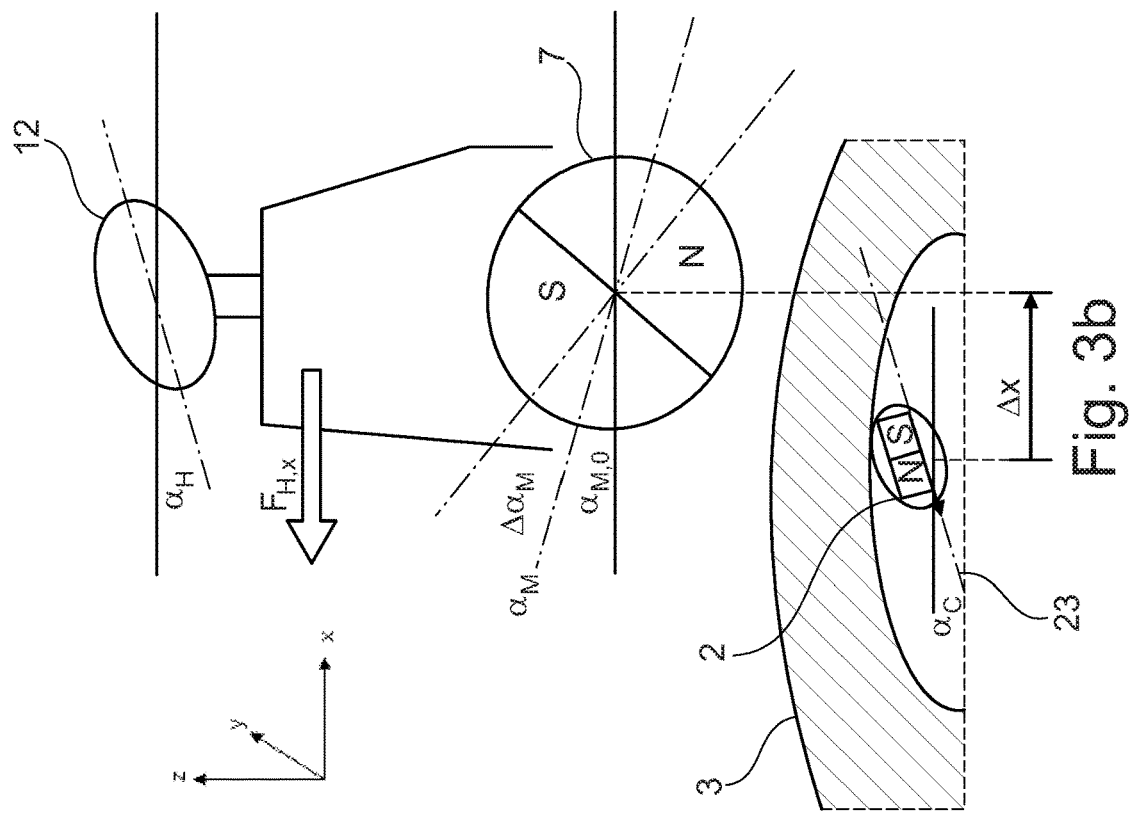
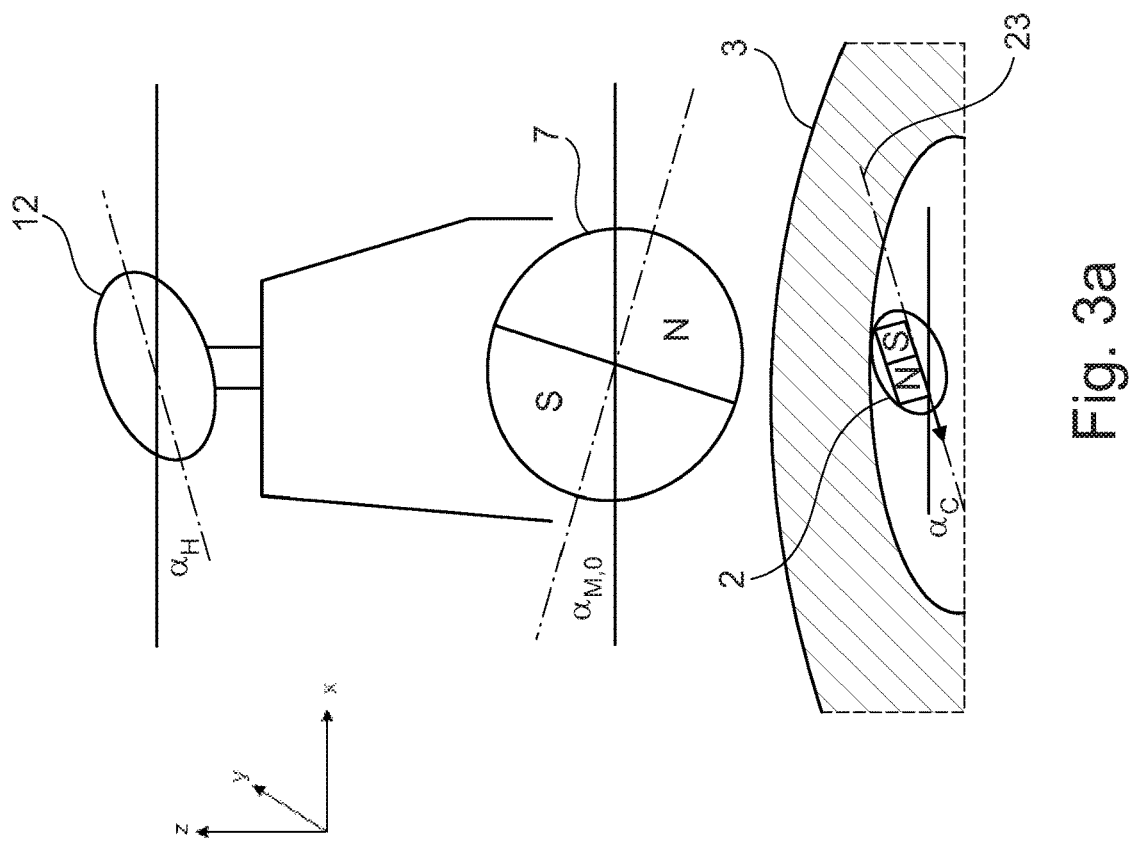

ENDOSCOPIC CAPSULE SYSTEM WITH HAPTIC FEEDBACK

This application is a U.S. National Phase application of PCT International Application No. PCT/EP2020/076623, filed Sep. 23, 2020, which claims the benefit of European Application No. 19199675.0, filed Sep. 25, 2019, both of which are incorporated by reference herein.

The present invention relates to an endoscopic capsule system for magnetically guiding an intracorporeal endoscopic capsule. The guiding device according to aspects of the invention will be described hereinafter by the example of an application in gastrointestinal medicine. However, the invention can also be conferred, in its full content, upon other fields of application in medicine, such as in the respiratory system, visceral surgery, arthroscopy or neurosurgery, or technical systems. Such technical system can be, for example, a tubing system in which the object to be controlled is provided.

BACKGROUND OF THE INVENTION

Magnetically driven endoscopic capsule systems are types of endoscopes in which preferably an endoscopic capsule but possibly also a probe or catheter is introduced into the patient's body by e.g. being swallowed by a patient in a pill- or capsule-like manner. After introduction, the endoscopic capsule is advanced in the intestinal tract substantially by the natural peristaltic motion. For influencing the movement and orientation of the swallowed endoscopic capsule, a magnet inside the endoscopic capsule, hereinafter referred to as capsular magnet, as well as an extracorporeal magnet outside of the patient's body, hereinafter referred to as magnetic effector, are provided.

Both the capsular magnet and the magnetic effector are adapted to generate a magnetic field of known polarization. For this purpose, both a solenoid and a permanent magnet as well as a combination of single or plural one of the said two possibilities are suitable. The device may also consist of plural permanent magnets or plural solenoids whose magnetic fields superpose to form a resulting magnetic field. The use of permanent magnets though entails the advantage of a simple capsule and effector structure while generating a relatively strong magnetic field, which is why they are especially suitable for medical use. Furthermore, a permanent magnet requires no energy supply to maintain the magnetic field compared to solenoids.

Nowadays, several different types of magnetic endoscopic capsule systems that have been specifically developed and designed for examining the oesophagus, stomach and small and large intestine are known. Thus, whereas the method was originally developed for the examination of small intestines, which had previously been difficult to access endoscopically, today all sections of the gastrointestinal tract can be examined by capsule endoscopy. Especially the inspection of the stomach and large intestine is clinically by far more significant than the inspection of the oesophagus and small intestine since the endoscopic check-up in the stomach and colon plays a crucial role for early detection of cancer.

According to current prior art, the movement and orientation of the swallowed magnetic endoscopic capsule can be either controlled through (pre-programmed) computer-controlled systems, so called robotic systems, or through manual guidance by an operator.

EP 2 347 699 A1 discloses for example a magnet driven capsule type endoscope with an intracorporeal magnetic endoscopic capsule and an extracorporeal, preferably permanently acting, magnet which is mounted to a computer-controlled robot arm. Due to the arrangement and orientation of the capsular magnet provided inside the endoscopic capsule, the endoscopic capsule can be tilted around its cross axis, rotated around its vertical axis and rolled around its longitudinal axis through interaction with the extracorporeal (permanent) magnet. In this way, control of the orientation of the endoscopic capsule around all three axes of its Cartesian coordinate system (x-, y-, z-axis) is provided.

According to EP 2 347 699 A1, the position and orientation of the extracorporeal permanent magnet is controlled via robotic actors. The robotic actors are in turn controlled by a computer, which receives sensor signals/feedback signals from a position sensor integrated in the endoscopic capsule and from an operator-machine interface through which an operator can enter control instructions for moving the endoscopic capsule. These sensor signals are then processed by the computer and converted into correcting movements of the extracorporeal magnet which are carried out by the robotic actors, and which cannot be directly influenced by the operator and facilitate maintaining the relative position between the endoscopic capsule and the extracorporeal permanent magnet within an optimum range for implementing the control instructions entered by the operator. In other words, by direct information feedback between the endoscopic capsule and the robot arm a control of the position and the orientation of the endoscopic capsule intuitive and predictable to the controlling person can be obtained. For a complete understanding of the structure/assembly and functioning of the endoscopic capsule according to the present invention, reference is made here to the endoscopic capsule disclosed in EP 2 347 699 A1.

The magnet driven capsule type endoscope disclosed in EP 2 347 699 A1, however, has the drawback that the computer-controlled robot arm for guiding of the endoscopic capsule can perform also movements which might result in a collision with and without action of force on a patient's body and thus in actions endangering the patient or the controlling person upon his/her body. In other words, robots of conventional conception are easily capable of fatally injuring a person or damaging neighbouring objects in the case of a wrong movement.

During application of the magnet driven capsule type endoscope on the patient, it might furthermore occur that the operator controlling/guiding/moving the position and orientation of the extracorporeal permanent magnet and thus also of the magnetic endoscopic capsule by entering control instructions into the computer interrupts the present magnetic field unconsciously due to an excessive large distance of the extracorporeal permanent magnet and the magnetic endoscopic capsule relative to each other. Accordingly, the magnetic endoscopic capsule can no longer be guided by the extracorporeal permanent magnet and remains at the location in the gastrointestinal tract where the magnetic field was last present, at least if the influence of natural peristaltic motions is not taken into account. In this case, the operator first has to restore the magnetic field between the extracorporeal permanent magnet and the magnetic endoscopic capsule. Therefore, the operator needs to guide the robot arm to which the extracorporeal permanent magnet is mounted above the abdominal wall of the patient until the endoscopic capsule reacts again to the motion of the extracorporeal permanent magnet. Such a situation is obviously very time-consuming and prolongs the procedure unnecessarily.

Furthermore, it might also be possible that the operator enters control instructions into the computer due to which the extracorporeal permanent magnet is moved/guided at a non-optimal distance to the endoscopic capsule. As a result, the endoscopic capsule has in general difficulties in moving/positioning or moves/positions itself only very slow, which prolongs the procedure and is at the same time inefficient. In summary, the operator of the magnet driven capsule type endoscope has no feeling for the magnetic force depending on the position of both magnetic components, which makes the practical application considerably more difficult.

In DE 10 2011 054 910 A1 a medical robot system for magnetically guiding an endoscopic capsule with an extracorporeal motor-driven positioning device having a maximum of three degrees of freedom is disclosed. The positioning device can be activated for the translation movement of a distal connecting interface of the positioning device, to which a magnetic end effector is connected/connectable. The magnetic end effector itself has a maximum of two degrees of freedom to be activated for the preferably rotary movement of a magnetic field generator with which the magnetic endoscopic capsule is controlled inside the patient's body.

In order to reduce the risk of injuries by robot-guided orientation of the extracorporeal magnetic field generator, specific degrees of freedom of the magnetic field generator are integrally encased or enclosed. Thus, the number of degrees of freedom of a robot-guided orientation of the magnetic field generator freely accessible from the outside is reduced in the robot system disclosed in DE 10 2011 054 910 A1. In this way, the function of the device is not restricted and the device can be used in the case of medical application in direct contact with the patient's body minimizing impacts on the patient's body, which are detrimental to the patient.

However, such a design of a robot system for magnetically guiding an endoscopic capsule is very complex and requires several manufacturing steps and a multitude of individual components, consequently increasing the manufacturing costs. In connection with this, the acquisition costs for hospitals or doctor's surgeries for such robot systems are also very high. In comparison to alternative endoscopic systems, which might deliver similar results at a lower price, such complex robot systems are rather uneconomical and can therefore establish themselves on the market only to a lesser extent.

Manually guided control of extracorporeal magnetic field generators has on the other hand the advantage that the structure of the device may exhibit minimum complexity. In other words, manual guidance of an extracorporeal magnetic field generator requires less components than robotic systems in order to realize the same function. Along with this, manufacturing is easier and related costs are lower.

Furthermore, the operator gets a permanent information feedback on the motion parameters and especially collisions with and without action of force upon a patient's body by manual orientation of the extracorporeal magnetic field generator by at least his/her haptic sense. Thus, actions endangering the patient are precluded in the first place when orientating the magnetic field generator.

In view of the prior art, it is an object of the invention to provide an endoscopic capsule system with magnetic characteristics exhibiting higher functionality. It is a particular object of the invention to improve the positioning capability of the endoscopic capsule system, especially by permitting a conscious controllability of the orientation of the endoscopic capsule, and to increase the examination accuracy and minimize the necessary application duration in this way.

This object is achieved by an endoscopic capsule system comprising the features of claim 1. Advantageous further developments of the invention are the subject matter of dependent claims.

Accordingly, it is not only the core of the invention to define or determine a position and/or an orientation of the endoscopic capsule relative to the magnetic effector as proposed by the prior art, but to generate counter forces and/or counter moments or braking forces via a force and/or moment generation device or a braking device depending on the actually defined or determined position and/or orientation of the endoscopic capsule relative to the effector to counteract a moving force manually applied by an operator to an extracorporeal guiding and moving apparatus of the endoscopic capsule system used for controlling the capsule.

In other words, too fast or sudden moving/guiding of the extracorporeal guiding and moving apparatus having the effector mounted at one end portion or moving/guiding of the extracorporeal guiding and moving apparatus in case the distance between magnetic effector and endoscopic capsule is too large results in an interruption of the magnetic field between the endoscopic capsule and the magnetic effector and leads therefore to loss of controllability of the endoscopic capsule, as previously described. By (continuously) defining/determining the position and/or the orientation of the endoscopic capsule relative to the effector, conclusions can be drawn about the manual displacement of the extracorporeal guiding and moving apparatus and/or the effector carried out by an operator. Based thereon, counter forces and/or counter moments or braking forces are generated to counteract the manual displacement of the extracorporeal guiding and moving apparatus and/or the effector carried out by the operator. In this way, the operator receives a haptic feedback due to the generated counter forces and/or counter moments or braking forces, indicating him/her that further displacement of the extracorporeal guiding and moving apparatus and/or the effector may lead to an interruption of the magnetic field between the endoscopic capsule and the magnetic effector. Due to the generated haptic feedback, the operator receives also information in which direction the endoscopic capsule will be lost if displacement of the extracorporeal guiding and moving apparatus and/or the effector is continued. In this way, unconscious loss of the endoscopic capsule during application caused by the interruption of the magnetic field is avoided and controllability of the endoscopic capsule improved.

In addition, general handling of the system is made more efficient when compared to prior art. For example, since the generated haptic feedback is dependent on the displacement between the magnetic effector and the magnetic endoscopic capsule, the operator may perceive the operation of the extracorporeal guiding and moving apparatus and/or the effector in a way that can be compared to a rubber band-like connection between the effector and the endoscopic capsule; with increasing displacement between the effector and the endoscopic capsule, the counter force generated by the haptic feedback is increasing, as if a rubber band is being stretched and produces an increasing counter force. This rubber band-like effect is produced/simulated by the system through an appropriate interpretation of sensor data and resulting control of actuators to achieve respective haptic feedback forces. Since, obviously, no rubber band is actually included in the system as it would have to penetrate the patient's skin, this control principle may be described as "virtual rubber band" between the magnetic effector and the magnetic endoscopic capsule.

In detail, an endoscopic capsule system is provided that comprises an endoscopic capsule having magnetic characteristics and being adapted to get introduced into a hollow organ of a patient's body; an extracorporeal guiding and moving apparatus for the endoscopic capsule which has a moveable multi-hinged cantilever arm which is at one end portion pivotably mounted at a support stand and which comprises an effector having magnetic characteristics and being pivotably mounted at the other free end portion of the cantilever arm for trailing, rotating, yawing and/or pitching the endoscopic capsule in accordance with the actual movement of the effector; and a controller device being designed and adapted to define the position and orientation of the endoscopic capsule relative to the effector. In accordance with the invention, a force and/or moment generation device or a braking device is further provided being adapted to influence the extracorporeal guiding and moving apparatus at least with respect to pre-selected movements of the cantilever arm and/or the effector, the force and/or moment generation device or the braking device being connected to the controller device to generate counter forces and/or counter moments or braking forces against moving forces that are manually applied to the cantilever arm and/or effector in accordance with the actually defined position and/or orientation of the endoscopic capsule relative to the effector.

In order to control and generate these counter forces and/or counter moments or braking forces against moving forces that are manually applied to the cantilever arm and/or effector, a correction angle of a tilt angle of the endoscopic capsule and/or a roll angle of the endoscopic capsule serve as measure for the counter forces and/or counter moments or the braking forces against moving forces that are manually applied to the cantilever arm and/or effector.

The counter forces and/or counter moments or the braking forces against moving forces that are manually applied to the cantilever arm and/or effector, which represent the haptic feedback for the operator, may be generated in different ways at the guiding and moving apparatus. For instance, the counter forces and/or counter moments against moving forces that are manually applied to the cantilever arm and/or effector can be generated by at least one torque-controlled actuator of the cantilever arm. As an alternative, the braking forces against moving forces that are manually applied to the cantilever arm and/or effector can be generated by means of brake linings on a brake disc.

For efficiently defining or determining the position and/or orientation of the endoscopic capsule and the effector, the endoscopic capsule system may be provided with several sensors. According to another aspect of the invention, the position and/or the orientation of the effector may be defined or determined by at least one angle sensor. The position and/or the orientation of the endoscopic capsule may be defined by an inertial sensor provided inside the endoscopic capsule.

The extracorporeal guiding and moving apparatus may be provided with a rotatable and tiltable handle/joystick with which the position and/or the orientation of the effector is manually adjustable. Manual rotation of the handle/joystick, which results in yawing of the magnetic effector, is thereby transferred mechanically to a holding structure, i.e. in form of a holding fork, of the magnetic effector and takes place without abutment/stop/limit. Moreover, the handle/joystick has a freedom of movement of approximately ±80° when tilted manually. The handle/joystick is besides also designed to maintain the manually adjusted angle position of the effector when released by the operator. In this way, the last position/orientation of both the handle/joystick and the effector is maintained.

For vertical movement of the extracorporeal guiding and moving apparatus in order to move the effector towards or away from the patient's abdominal wall, the multi-hinged cantilever arm of the extracorporeal guiding and moving apparatus may have a parallelogram arm with a spring element or spring-damper element. The spring element or spring-damper element is thereby used for weight compensation of the effector so that during movement of the effector in vertical direction no lifting work has to be carried out, but only the force for acceleration and braking has to be applied. Furthermore, the spring element or spring-damper element can be designed to compensate for the weight of the operator's arm, in order to enable the operator to rest his/her arm on the extracorporeal guiding and moving apparatus in a way that allows continuous operation of the extracorporeal guiding and moving apparatus without accelerated muscle fatigue in a rather relaxed manner. According to another aspect of the invention, the handle/joystick further has a member designed to support the operator's arm/upon which the operator can rest the weight of his/her arm. In order to preserve the fine motor manipulation of the handle's/joystick's angular degrees of freedom (e.g. tilting, yawing) while resting the weight of the arm on this member, at least one angular degree of freedom of the handle/joystick is disconnected/is working independent from said member. To increase the ease of use of the endoscopic capsule system, the parallelogram arm may also be actuated in a torque-controlled manner.

According to another aspect of the invention, the parallelogram arm may be further designed so as to lead the effector into a position in which the magnetic link between the effector and the endoscopic capsule is interrupted when the handle/joystick is released. In other words, upon release of the handle/joystick by the operator, for example due to an application interruption, the effector is automatically moved away from the abdominal wall of the patient and the endoscopic capsule in vertical direction by means of the parallelogram arm until the present magnetic field between effector and endoscopic capsule is interrupted.

Alternatively, the parallelogram arm may also be designed so as to lead the effector into a position in which the effector is located directly above the endoscopic capsule when the handle/joystick is released. This means that upon release of the handle/joystick by the operator, the effector is moved in vertical direction and within the present magnetic field between effector and endoscopic capsule as close as possible to the abdominal wall section of the patient directly located above the endoscopic capsule by means of the parallelogram arm.

The endoscopic capsule system may also be fully automated, thus making the general handling of the system more convenient. In order to realize this, the rotating actuation of the handle/joystick may be designed to be actuated in a torque-controlled manner.

According to a further aspect of the invention, the effector may be actuated to roll without abutment/stop/limit. In this way, rolling of the effector in response to tilting of the handle/joystick at a 360 degree angle and beyond is made possible. However, rolling of the effector is not limited to a torque-controlled actuation. Instead, according to an aspect of the invention the magnetic effector may be actuated in a displacement-controlled or angle-driven manner.

It should be expressly noted that the above aspects can solve the object of the invention individually or in any combination with each other and should therefore be claimable individually or in any combination within the scope of this application.

DESCRIPTION OF FIGURES

Hereinafter, the invention will be described in detail by way of a preferred embodiment with reference to the accompanying figures, in which:

FIGS. 3a and 3b illustrate a control mechanism of the tilt angle of the endoscopic capsule according to the invention.

FIG. 1 shows the entire endoscopic capsule system 1 during usual clinical application. The endoscopic capsule system 1 comprises an endoscopic capsule 2 which has already been introduced into the gastrointestinal tract of a schematically represented patient 3; an extracorporeal guiding and moving apparatus 4 which has a moveable multi-hinged cantilever arm 5 which is at one end portion pivotally mounted at a support stand 6 and which comprises a magnetic effector 7 being pivotally mounted at the other free end portion of the cantilever arm 5; and a controller device 8 being designed and adapted to define or determine the position and the orientation of the endoscopic capsule 2 relative to the effector 7. Moreover, the endoscopic capsule system 1 is equipped with a force and/or moment generation device or a braking device 9, which is adapted to influence the extracorporeal guiding and moving apparatus 4 at least with respect to pre-selected movements of the cantilever arm 5 and/or the effector 7. The force and/or moment generation device or the braking device 9 is furthermore connected to the controller device 8 and generates counter forces and/or counter moments or braking forces against moving forces that are manually applied to the cantilever arm 5 and/or effector 7 in accordance with the actually defined or determined position and/or orientation of the endoscopic capsule 2 relative to the effector 7.

Figure 1:
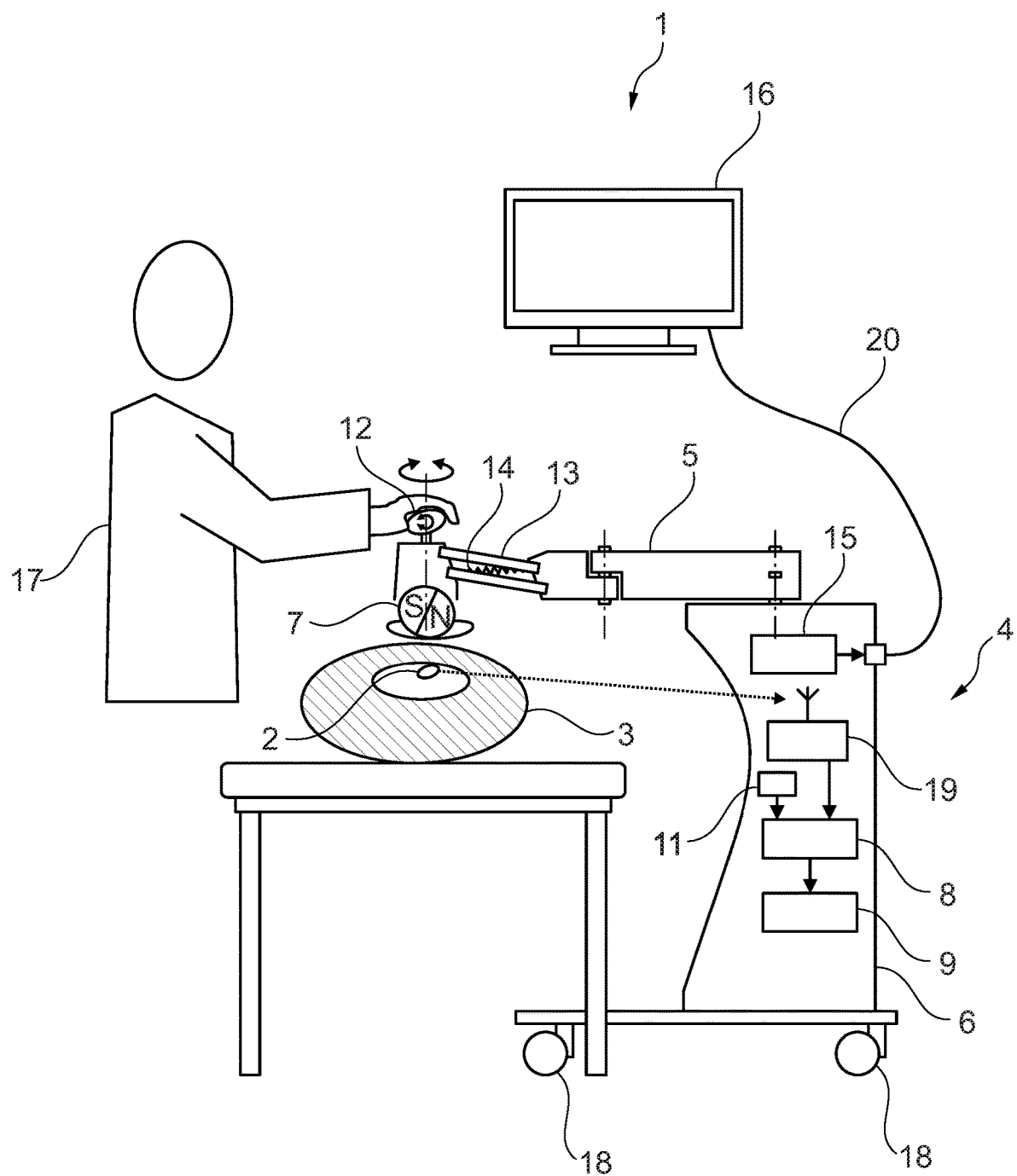
FIG. 1 schematically shows a clinical application of the endoscopic capsule system and a corresponding control according to the invention, FIG. 2 schematically shows the basic structure of the extracorporeal guiding and moving apparatus with corresponding actuators and sensors.

In order to enable manual movement/guidance of the effector 7 by an operator 17, a handle/joystick 12 is provided at the end portion of the cantilever arm 5 to which the effector 7 is mounted. The handle/joystick 12 is connected to a holding structure, e.g. in the shape of a holding fork, of the effector 7 not further shown, which enables transmission of movements of the handle/joystick 12 to the effector 7. Accordingly, tilting and/or rotating of the handle/joystick 12 results in rolling and/or yawing of the effector 7.

The multi-hinged cantilever arm 5 itself is designed to have several portions, preferably three portions, in order to provide movement of the effector 7 around all three axes of the Cartesian coordinate system (x-, y-, z-axis). The portion of the cantilever arm 5 enabling movement in vertical direction (z-axis) is designed in form of a parallelogram arm 13 comprising a spring element or spring-damper element 14 for compensating the weight of the effector 7. The spring element or spring-damper element 14 can be furthermore designed to compensate the weight of the operator's 17 arm, in order to enable the operator 17 to rest his/her arm on the extracorporeal guiding and moving apparatus 4 in a way that allows continuous operation of the extracorporeal guiding and moving apparatus 4. Besides, the handle/joystick 12 can have a member not further shown, upon which the operator 17 can rest the weight of his/her arm. In order to preserve the fine motor manipulation of the handle's/joystick's 12 angular degrees of freedom (e.g. tilting, yawing) while resting the weight of the operator's 17 arm on this member, at least one angular degree of freedom of the handle/joystick 12 is working independent from said member. As previously mentioned, the cantilever arm 5 is at its other end portion pivotally mounted to the support stand 6. The end of the support stand 6 being in contact with the floor may have rollers/wheels 18 through which the extracorporeal guiding and moving apparatus 4 is made mobile.

The endoscopic capsule system is further provided with a video processor 15, which receives wirelessly transmitted image data of the gastrointestinal tract recorded by the endoscopic capsule 2 and processes these. Visualisation of these data in form of a real-time video is provided through the connection of the video processor 15 to an endoscopic screen 16 via an electric cable 20. In this way, the operator 17 is able to monitor the tilt and/or viewing direction of the endoscopic capsule 2 and to adjust it as required by tilting and/or rotating the handle/joystick 12.

Moreover, in a preferred embodiment, both the endoscopic capsule 2 and the extracorporeal guiding and moving apparatus 4 are equipped with sensors for defining the position and/or the orientation of the endoscopic capsule 2 and the magnetic effector 7, respectively. While the endoscopic capsule 2 is provided with an inertial sensor not further shown, the extracorporeal guiding and moving apparatus 4 is equipped with at least one, but preferably with several angle sensors 11. When the operator 17 manually applies moving forces to the cantilever arm 5 and/or the effector 7 via the handle/joystick 12, the angle sensors 11 determine/record the actual position and/or the orientation of the effector 7. These positional and/or orientational data of the effector 7 measured by the angle sensors 11 are subsequently transmitted to the controller device 8. At the same time, the inertial sensor arranged inside the endoscopic capsule 2 transmits data about the position and/or the orientation of the endoscopic capsule 2 in form of radio signals to a radio frequency receiver 19 arranged within the extracorporeal guiding and moving apparatus 4. Like the positional and/or orientational data of the effector 7, the radio signals received by the radio frequency receiver 19 are transmitted to the controller device 8. The controller device 8 processes these positional and/or orientational data of the endoscopic capsule 2 and the magnetic effector 7 and controls/regulates based thereon the generation of counter forces and/or counter moments or braking forces via the force and/or moment generation device or the braking device 9. In other embodiments, the sensors inside the endoscopic capsule 2 may be any sensor or configuration of sensors that allow concluding on the position and orientation of the endoscopic capsule 2 at least in respect to the effector 7. The sensor in the extracorporeal guiding and moving apparatus 4 may be any sensor or configuration of sensors that allow concluding on the position and orientation of the effector 7 at least in respect to the endoscopic capsule 2.

Figure 2:
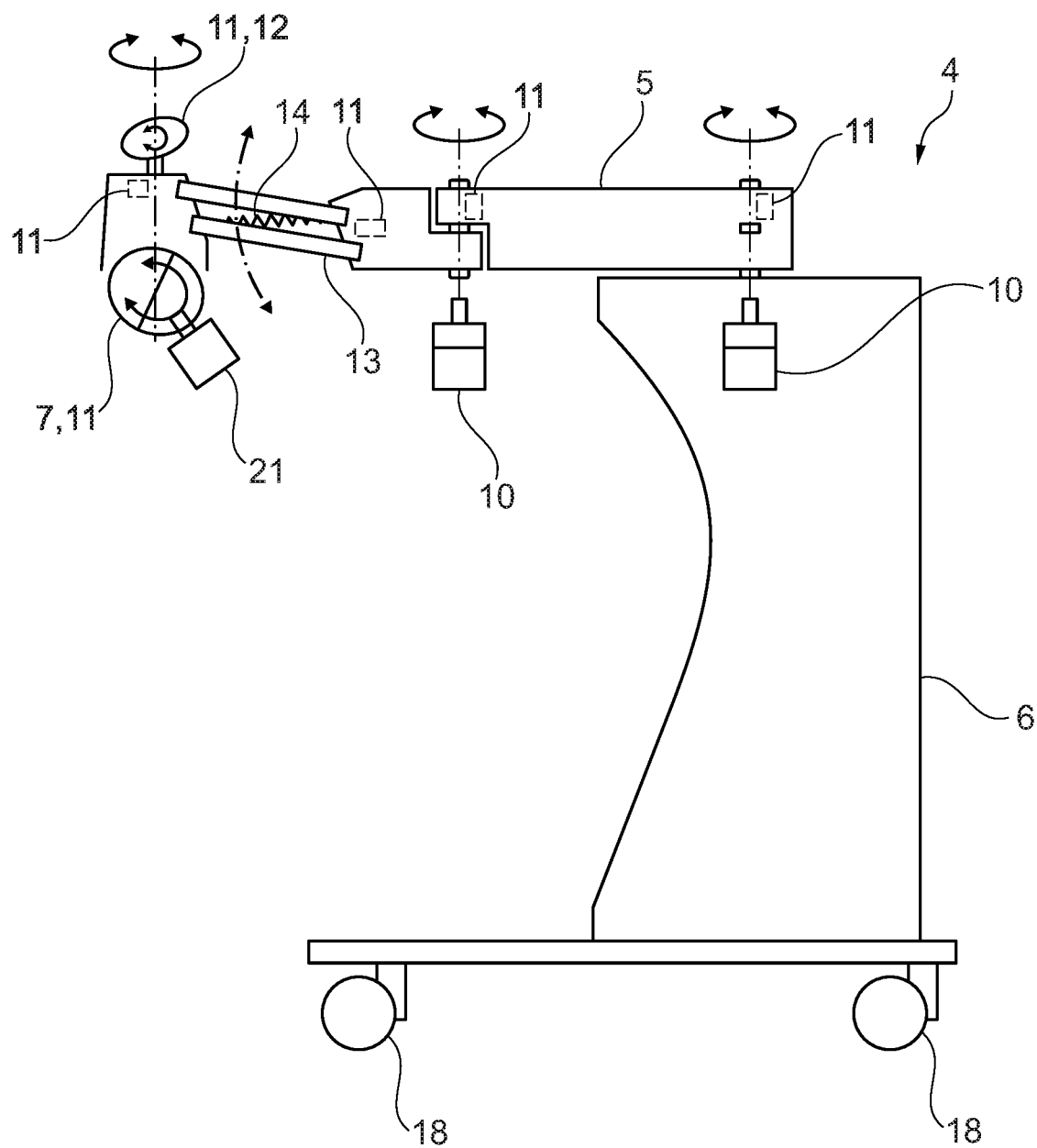

In FIG. 2 the basic structure of the extracorporeal guiding and moving apparatus 4 with corresponding actuators and sensors is schematically illustrated in a preferred embodiment. The basic structure and the reference numerals from the extracorporeal guiding and moving apparatus 4 shown in FIG. 1 remain unchanged, so that in the following only differences between the extracorporeal guiding and moving apparatus 4 of FIG. 1 and FIG. 2 are emphasized. FIG. 2 shows the angle sensors 11, which are merely indicated in FIG. 1, arranged at concrete positions over the cantilever arm 5 and the end portion of the cantilever arm 5 to which the effector 7 is mounted. The extracorporeal guiding and moving apparatus 4 is preferably provided with six angle sensors 11, each determining individual positions/orientations of the cantilever arm 5 and the magnetic effector 7 in order to enable precise determination of the position and/or the orientation of the effector 7.

In particular, one angle sensor 11 for each hinge of the multi-hinged cantilever arm 5 and thus for every movement axis of the cantilever arm 5 (x-, y-, z-axis) is provided, determining the angle and in this way the position of each portion of the cantilever arm 5. Furthermore, the magnetic effector 7 itself is equipped with an angle sensor 11, which due to the fact that the effector 7 is able to roll without abutment/stop/limit permits the determination of an unlimited angle area. Moreover, the handle/joystick 12 is provided with an angle sensor 11 enabling determination of the orientation of the effector 7 by measuring the angle of the handle/joystick 12 during tilting. The last angle sensor 11 is provided to determine the rotation angle of the handle/joystick 12, thus determining the yaw angle of the effector 7. This angle sensor 11 is similarly to the angle sensor 11 of the effector 7 designed to determine an unlimited angle area.

As previously described, the controller device 8 controls the force and/or moment eneration device or the braking device 9 based on the positional and/or orientational data of the endoscopic capsule 2 and the effector 7 measured by the inertial sensor and angle sensors 11. In general, the force and/or moment generation device or the braking device 9 is realized by different components able to generate counter forces and/or counter moments or braking forces. In FIG. 2, the counter forces and/or counter moments against moving forces manually applied to the cantilever arm 5 and/or the magnetic effector 7 are generated by torque-controlled actuators 10 of the cantilever arm 5. For example by applying counter moments to the respective actuators 10, a corresponding counter force can be generated, which the operator 17 perceives as haptic feedback. Alternatively or additionally, disc brakes or other types of brakes can be used to generate proper braking forces against moving forces manually applied to the cantilever arm 5 and/or the effector 7. Hence, the counter forces and/or counter moments or braking forces can be generated in different ways. Although not shown in FIG. 2, the parallelogram arm 13 can also be actuated in a torque-controlled manner, thus increasing the ease of use of the endoscopic capsule system 1.

In addition to the torque-controlled actuators 10 of the cantilever arm 5, another actuator 21 is provided at the magnetic effector 7 as shown in FIG. 2. However, the actuator 21 of the effector 7 is not a torque-controlled actuator but instead a displacement-controlled or angle-driven actuator 21 enabling the effector to roll without abutment/stop/limit. In other embodiments, the sensors inside the endoscopic capsule 2 may be any sensor or configuration of sensors that allow concluding on the position and orientation of the endoscopic capsule 2 at least in respect to the effector 7. The sensor in the extracorporeal guiding and moving apparatus 4 may be any sensor or configuration of sensors that allow concluding on the position and orientation of the effector 7 at least in respect to the endoscopic capsule 2.

Usually the endoscopic capsule 2 follows the movement/guiding of the effector 7 unhindered which is why in this case no counter forces and/or counter moments or braking forces are generated by the force and/or moment generation device or the braking device 9. However, if the movement of the endoscopic capsule 2 no longer corresponds to the movement of the effector 7, i.e. if the endoscopic capsule 2 cannot follow the effector 7 because the hollow organ prevents movement in x- or y-direction, a deviation in position and/or orientation of the endoscopic capsule 2 and effector 7 relative to each other occurs. In this case counter forces and/or counter moments or braking forces are generated by the force and/or moment generation device or the braking device 9, thus indicating the operator 17 in form of the generated haptic feedback the current deviation. In order to control/regulate the haptic feedback generated due to the deviation between the endoscopic capsule 2 and the effector 7, the present invention provides two control mechanisms.

The control mechanism shown in FIGS. 3a and 3b serves for controlling/regulating the tilt angle of the endoscopic capsule 2 upon a manual displacement of the effector 7 by the operator 17 via the handle/joystick 12 for a linear motion of the endoscopic capsule 2 in the x-direction of the horizontal plane. The compensating movement in order to avoid tilting of the endoscopic capsule 2 is represented in FIG. 3b.

Concretely speaking, FIG. 3a shows the orientation of the endoscopic capsule 2 in the event that the magnetic effector 7 is provided directly above the same, which hereinafter will be referred to as home position of the magnetic effector 7. Accordingly, the endoscopic capsule 2 orients itself so that the polarization (N/S) of the capsular magnet is anti-parallel to that of the effector 7. At the same time, the control of the tilt angle of the effector 7 is, according to the present invention, designed in a way that a tilt angle of the handle/joystick 12 (with respect to a horizontal plane), hereinafter referred to as $\alpha_H$, corresponds to a tilt angle of the endoscopic capsule 2 (with respect to a horizontal plane), hereinafter referred to as $\alpha_C$:

$$\alpha_H = \alpha_C \tag{1}$$

In contrast to that, $\alpha_H$ is due to the anti-parallel polarization of the endoscopic capsule 2 and the effector 7 to each other related to a tilt angle $\alpha_M$, $\alpha_{M,0}$ of the effector 7 in its home position as follows:

$$\alpha_M = \alpha_{M,0} - \alpha_H \tag{2}$$

FIG. 3b shows the effect on the orientation of the effector 7 when the effector 7 is manually displaced via the handle/joystick 12 in the x-direction of the horizontal plane relative to the endoscopic capsule 2, starting from the home position as shown in FIG. 3a, so that the x-position of the effector 7 and the x-position of the endoscopic capsule 2 deviate from each other by a difference Δx in x-direction. A displacement of the effector 7 via the handle/joystick 12 in the x-direction of the horizontal plane would usually result in a tilting movement of the endoscopic capsule 2 due to the present circular magnetic field. However, according to the present invention the change of position and/or orientation of the magnetic effector 7 is as previously described continuously registered by the angle sensors 11 of the extracorporeal guiding and moving apparatus 4. These sensor data are simultaneously made available to the controller device 8 which in case of a deviation between the x-position of the effector 7 and the x-position of the endoscopic capsule 2 consequently controls/regulates the tilt angle $\alpha_M$ of the magnetic effector 7 such that equation (1) remains valid and tilting of the endoscopic capsule 2 is prevented. Therefore, $\alpha_M$ is continuously corrected by a correction angle $\Delta\alpha_M$. Based thereon, the actual tilt angle of the effector 7 $\alpha_M$ is represented by the sum of the tilt angle of the effector 7 in its home position $\alpha_{M,0}$ and the correction angle of the tilt angle of the effector 7 $\Delta\alpha_M$:

$$\alpha_M = \alpha_{M,0} + \Delta\alpha_M \quad (3)$$

In other words, $\alpha_H$ represents the target tilt angle of the endoscopic capsule 2, which is adjusted manually by the operator 17 and is measured by means of the angle sensor 11 provided in the handle/joystick 12. $\alpha_C$ represents on the other side the actual tilt angle of the endoscopic capsule 2, which is adjusted by means of the magnetic field between the endoscopic capsule 2 and the effector 7 and is measured by means of the inertial sensor provided inside the endoscopic capsule 2. In order to ensure that $\alpha_C$ corresponds to $\alpha_H$, $\alpha_M$ is continuously determined by means of the angle sensors 11 and accordingly adjusted by means of the actuators 10, 21. This relationship gives rise to the following equation used for the control/regulation of the tilt angle $\alpha_C$ of the endoscopic capsule 2:

$$\alpha_{M,n+1} = \alpha_{M,n} + f(\alpha_{C,n} - \alpha_{H,n}) \quad (4)$$

Based on the foregoing context, $\Delta\alpha_M$ can be seen as measure for the manual displacement of the effector 7 in the x-direction of the horizontal plane $\Delta x$ even though the precise displacement $\Delta x$ is not known due to the unknown distance between endoscopic capsule 2 and magnetic effector 7 in vertical direction $\Delta z$. Accordingly, $\Delta\alpha_M$ is used as measure for the control and generation of the haptic counter force in the x-direction of the horizontal plane $F_{H,x}$:

$$F_{H,x} \rightarrow f(\Delta\alpha_M) \quad (5)$$

In practice, the previously described control method causes a delay due to the corrective readjustment of the effector 7 and the transmission of the positional and/or orientational data of the endoscopic capsule 2 via radio signals. However, due to the slow movements to be expected from the operator 17 during application, this is rather irrelevant.

Figure 4B:
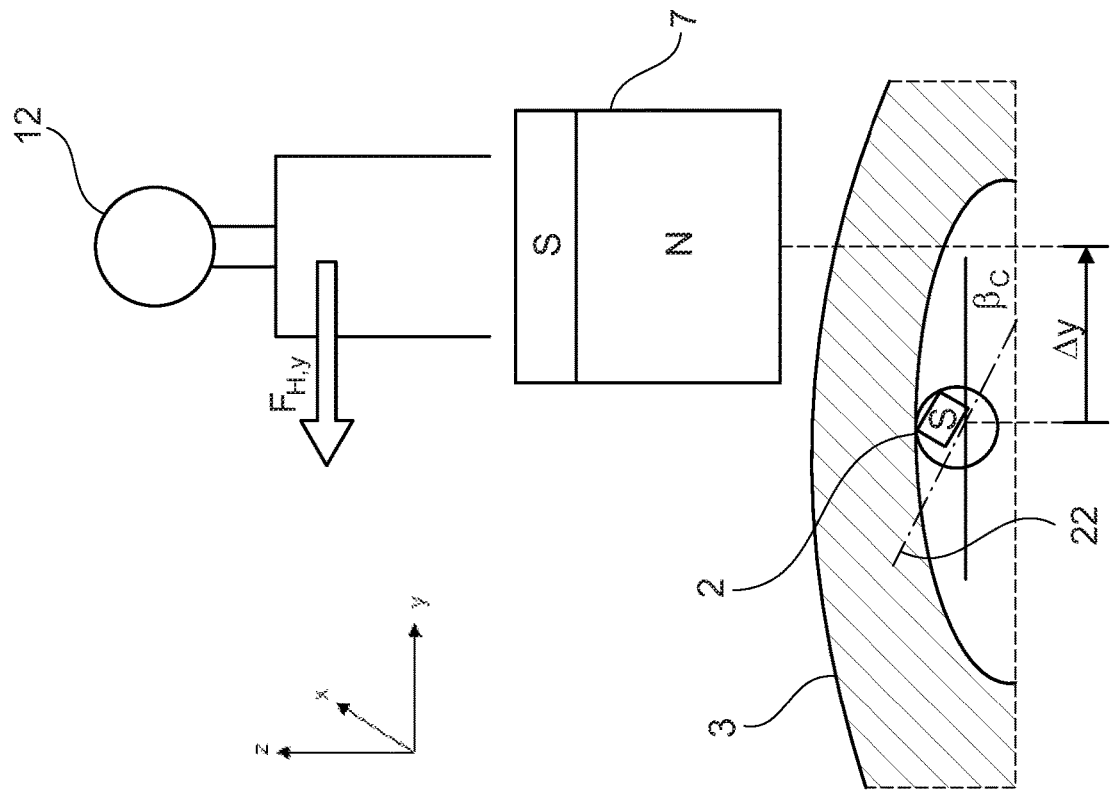
FIGS. 4a and 4b illustrate a control mechanism of the roll angle of the endoscopic capsule according to the invention.
Figure 4A:
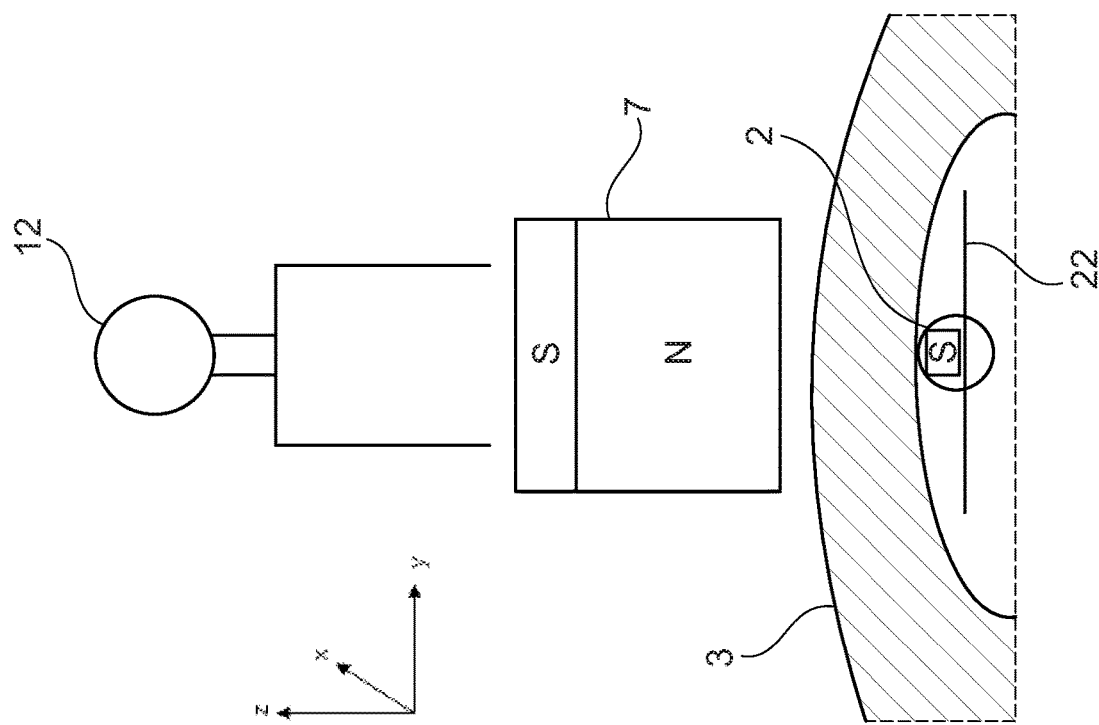

FIGS. 4a and 4b show another control mechanism of the endoscopic capsule 2 according to the invention, which serves for orienting the effector 7 along its y-axis by manual displacement of the effector 7 via the handle/joystick 12 vertically above the endoscopic capsule 2 such that the y-axis 22 of the endoscopic capsule 2 is provided in the horizontal plane.

FIG. 4a shows the orientation of the endoscopic capsule 2 as well as its y-axis 22 in case that the magnetic effector 7 is provided vertically above the same and the polarization of the magnetic effector 7 is vertical. The endoscopic capsule 2 orients itself such that the polarization of the capsular magnet provided inside the endoscopic capsule 2 is anti-parallel to that of the extracorporeal permanent magnet 13, i.e. the y-axis 22 of the endoscopic capsule 2 is oriented horizontally and no rolling of the endoscopic capsule 2 occurs. According to the invention, the endoscopic capsule 2 is designed to have a stabile horizon, which means rolling of the endoscopic capsule 2 around its longitudinal axis/x-axis 23 is avoided.

FIG. 4b shows the effect on the orientation of the endoscopic capsule 2 when the magnetic effector 7 is manually displaced along its y-axis relative to the endoscopic capsule 2, i.e. in the sideward direction of the endoscopic capsule 2, starting from the situation as shown in FIG. 4a. In this case, the endoscopic capsule 2 starts to roll around its longitudinal axis/x-axis 23 so that a so called roll angle $\beta_C$ of the endoscopic capsule 2 forms between the y-axis 22 of the endoscopic capsule 2 and the horizontal plane. This change of orientation is equally registered by the inertial sensor inside the endoscopic capsule 2 and the angle sensors 11 of the extracorporeal guiding and moving apparatus 4, and appropriate sensor data are made available to the controller device 8. Similar to $\Delta\alpha_M$ in FIG. 3b, $\beta_C$ serves as measure for the manual displacement of the effector 7 in the y-direction of the horizontal plane $\Delta y$, and is used as measure for calculation and generation of the haptic counter force in the y-direction of the horizontal plane $F_{H,y}$, which counteracts the rolling of the endoscopic capsule 2 around its longitudinal axis/x-axis 23:

$$F_{H,y} \rightarrow f(\beta_C) \quad (6)$$

In contrast to the control/regulation mechanism of the tilt angle $\alpha_C$, the roll angle $\beta_C$ is not directly controlled and adjusted by means of a correction angle. Instead, the operator 17 of the endoscopic capsule system 1 is able to compensate such a displacement of the magnetic effector 7 in the y-direction of the horizontal plane $\Delta y$ intuitively due to the feedback obtained via the generated haptic counter force in the y-direction of the horizontal plane $F_{H,y}$. During practical application of the endoscope capsule system 1 situations such as manoeuvring of the endoscopic capsule 2 in a deep left flexure of the colon might occur in which it is useful to position the magnetic effector 7 laterally to the endoscopic capsule 2 in order to effect a desired force on the endoscopic capsule 2 via the magnetic field. In this case, the operator 17 consciously accepts and moreover controls the rolling of the endoscopic capsule 2 around its longitudinal axis/x-axis 23 and the generated counter force in the y-direction of the horizontal plane $F_{H,y}$ in order to bring the endoscopic capsule 2 in the desired position.

In summary, the invention therefore concerns an endoscopic capsule system 1 comprising an endoscopic capsule 2 having magnetic characteristics and being adapted to get introduced into a hollow organ of a patient's body 3; an extracorporeal guiding and moving apparatus 4 for the endoscopic capsule 2 which has a moveable multi-hinged cantilever arm 5 which is at one end portion pivotably mounted at a support stand 6 and which comprises an effector 7 having magnetic characteristics and being pivotably mounted at the other free end portion of the cantilever arm 5 for trailing, rotating, yawing and/or pitching the endoscopic capsule 2 in accordance with the actual movement of the effector 7; and a controller device 8 being designed and adapted to define the position and orientation of the endoscopic capsule 2 relative to the effector 7. According to the invention, such an endoscopic capsule system 1 comprises further a force and/or moment generation device or a braking device 9, which is adapted to influence the extracorporeal guiding and moving apparatus 4 at least with respect to pre-selected movements of the cantilever arm 5 and/or the effector 7, the force and/or moment generation device or braking device 9 being connected to the controller device 8 to generate counter forces and/or counter moments or braking forces against moving and/or guiding forces that are manually applied to the cantilever arm 5 and/or effector 7 in accordance with the actually defined position and/or orientation of the endoscopic capsule 2 relative to the effector 7.

LIST OF REFERENCE NUMERALS

1 Endoscopic capsule system
2 Endoscopic capsule
3 Patient's body
4 Extracorporeal guiding and moving apparatus 5 Cantilever arm
6 Support stand
7 Effector
8 Controller device
9 Force and/or moment generation device or braking device
10 Actuator of the cantilever arm
11 Angle sensor
12 Handle/joystick
13 Parallelogram arm
14 Spring element or spring-damper element
15 Video processor
16 Endoscopic screen
17 Operator
18 Rollers/wheels
19 Radio frequency receiver
20 Electric cable
21 Actuator of the effector
22 Y-axis of the endoscopic capsule
23 X-axis of the endoscopic capsule
N North pole
S South pole
$\alpha_C$ Tilt angle of the endoscopic capsule
$\alpha_H$ Tilt angle of handle/joystick
$\alpha_M$ Tilt angle of effector
$\alpha_{M,0}$ Tilt angle of effector in its home position
$\Delta\alpha_M$ Correction angle of the tilt angle of effector
$\Delta x$ Displacement of effector in the x-direction of the horizontal plane
$F_{H,x}$ Counter force in the x-direction of the horizontal plane
$\beta_C$ Roll angle of the endoscopic capsule
$\Delta y$ Displacement of effector in the y-direction of the horizontal plane
$F_{H,y}$ Counter force in the y-direction of the horizontal plane
$\Delta z$ Distance between effector and endoscopic capsule in vertical direction

The invention claimed is:

1. An endoscopic capsule system comprising:
an endoscopic capsule having magnetic characteristics and being adapted to get introduced into a hollow organ of a patient's body;
an extracorporeal guiding and moving apparatus for guiding and moving the endoscopic capsule, said extracorporeal guiding and moving apparatus having a moveable multi-hinged cantilever arm, which is at one end portion pivotally mounted at a support stand and which comprises an effector having magnetic characteristics and being pivotally mounted at the other free end portion of the cantilever arm for trailing, rotating, yawing and/or pitching the endoscopic capsule in accordance with the actual movement of the effector;
a controller device being designed and adapted to define a position and/or an orientation of the endoscopic capsule relative to the effector; and
a force and/or moment generation device or a braking device being adapted to influence the extracorporeal guiding and moving apparatus at least with respect to pre-selected movements of the cantilever arm and/or the effector, the force and/or moment generation device or the braking device being connected to the controller device to generate counter forces and/or counter moments or braking forces against moving forces that are manually applied to the cantilever arm and/or effector in accordance with the actually defined position and/or orientation of the endoscopic capsule relative to the effector.

2. The endoscopic capsule system according to claim 1, wherein the counter forces and/or counter moments against moving forces that are manually applied to the cantilever arm and/or effector are generated by at least one torque-controlled actuator of the cantilever arm.

3. The endoscopic capsule system according to claim 1, wherein the braking forces against moving forces that are manually applied to the cantilever arm and/or effector are generated by means of brake linings on a brake disc.

4. The endoscopic capsule system according to claim 1, wherein the extracorporeal guiding and moving apparatus has a rotatable and tiltable handle/joystick with which the position and/or the orientation of the effector is manually adjusted.

5. The endoscopic capsule system according to claim 4, wherein the manually adjusted position and/or orientation of the effector is maintained when the handle/joystick is released.

6. The endoscopic capsule system according to claim 1, wherein the handle/joystick has a member upon which the operator can rest the weight of his/her arm, wherein at least one angular degree of freedom of the handle/joystick is working independent from said member.

7. The endoscopic capsule system according to claim 1, wherein the multi-hinged cantilever arm of the extracorporeal guiding and moving apparatus has a parallelogram arm with a spring element or spring-damper element.

8. The endoscopic capsule system according to claim 7, wherein the parallelogram arm is actuated in a torque-controlled manner.

9. The endoscopic capsule system according to claim 7, wherein the parallelogram arm leads the effector into a position in which the magnetic field is interrupted when the handle/joystick is released.

10. The endoscopic capsule system according to claim 7, wherein the parallelogram arm leads the effector into a position in which the effector is located directly above the endoscopic capsule when the handle/joystick is released.

11. The endoscopic capsule system according to claim 1, wherein the rotating actuation of the handle/joystick is actuated in a torque-controlled manner.

12. The endoscopic capsule system according to claim 1, wherein the effector is actuated to roll without abutment.

13. The endoscopic capsule system according to claim 12, wherein the effector is actuated in a displacement-controlled or angle-driven manner.

14. An endoscopic capsule system comprising:
an endoscopic capsule having magnetic characteristics and being adapted to get introduced into a hollow organ of a patient's body;
an extracorporeal guiding and moving apparatus for guiding and moving the endoscopic capsule, said extracorporeal guiding and moving apparatus having a moveable multi-hinged cantilever arm, which is at one end portion pivotally mounted at a support stand and which comprises an effector having magnetic characteristics and being pivotally mounted at the other free end portion of the cantilever arm for trailing, rotating, yawing and/or pitching the endoscopic capsule in accordance with the actual movement of the effector;
a controller device being designed and adapted to define a position and/or an orientation of the endoscopic capsule relative to the effector; and a force and/or moment generation device or a braking device being adapted to influence the extracorporeal guiding and moving apparatus at least with respect to pre-selected movements of the cantilever arm and/or the effector, the force and/or moment generation device or the braking device being connected to the controller device to generate counter forces and/or counter moments or braking forces against moving forces that are manually applied to the cantilever arm and/or effector in accordance with the actually defined position and/or orientation of the endoscopic capsule relative to the effector, wherein a correction angle of a tilt angle of the endoscopic capsule and/or a roll angle of the endoscopic capsule serve as measure for the counter forces and/or counter moments or the braking forces against moving forces that are manually applied to the cantilever arm and/or effector.

15. An endoscopic capsule system comprising:

an endoscopic capsule having magnetic characteristics and being adapted to get introduced into a hollow organ of a patient's body;

an extracorporeal guiding and moving apparatus for guiding and moving the endoscopic capsule, said extracorporeal guiding and moving apparatus having a moveable multi-hinged cantilever arm, which is at one end portion pivotally mounted at a support stand and which comprises an effector having magnetic characteristics and being pivotally mounted at the other free end portion of the cantilever arm for trailing, rotating, yawing and/or pitching the endoscopic capsule in accordance with the actual movement of the effector;

a controller device being designed and adapted to define a position and/or an orientation of the endoscopic capsule relative to the effector; and a force and/or moment generation device or a braking device being adapted to influence the extracorporeal guiding and moving apparatus at least with respect to pre-selected movements of the cantilever arm and/or the effector, the force and/or moment generation device or the braking device being connected to the controller device to generate counter forces and/or counter moments or braking forces against moving forces that are manually applied to the cantilever arm and/or effector in accordance with the actually defined position and/or orientation of the endoscopic capsule relative to the effector, wherein the position and/or the orientation of the effector is defined by at least one angle sensor and the position and/or the orientation of the endoscopic capsule is defined by an inertial sensor provided inside the endoscopic capsule.

* * * * *